(12) United States Patent
Harding

(10) Patent No.: US 8,617,365 B2
(45) Date of Patent: Dec. 31, 2013

(54) ELECTROCHEMICAL ASSAY DEVICE AND RELATED METHODS

(75) Inventor: Ian Harding, Somerville, MA (US)

(73) Assignee: AgaMatrix, Inc., Salem, NH (US)

(*) Notice: Subject to any disclaimer, the term of this patent is extended or adjusted under 35 U.S.C. 154(b) by 1668 days.

(21) Appl. No.: 10/908,664

(22) Filed: May 21, 2005

(65) Prior Publication Data

US 2005/0258036 A1 Nov. 24, 2005

Related U.S. Application Data

(60) Provisional application No. 60/521,555, filed on May 21, 2004.

(51) Int. Cl.
*G01N 33/487* (2006.01)

(52) U.S. Cl.
USPC ............ 204/403.01; 204/403.02; 204/403.03; 204/403.04; 204/403.05; 205/777.5; 205/778

(58) Field of Classification Search
USPC .............. 204/403.01–403.15; 205/777.5–778
See application file for complete search history.

(56) References Cited

U.S. PATENT DOCUMENTS

| 5,120,420 | A | * | 6/1992 | Nankai et al. ............ 204/403.11 |
| 5,437,999 | A | | 8/1995 | Diebold et al. |
| 5,695,947 | A | * | 12/1997 | Guo et al. .................... 435/11 |
| 6,071,391 | A | | 6/2000 | Gotoh et al. |
| 6,156,173 | A | | 12/2000 | Gotoh et al. |
| 6,416,641 | B1 | | 7/2002 | Ikeda et al. |
| 6,447,657 | B1 | * | 9/2002 | Bhullar et al. ............ 204/403.01 |
| 6,616,819 | B1 | | 9/2003 | Liamos et al. |
| 6,618,934 | B1 | | 9/2003 | Feldman et al. |
| 6,878,251 | B2 | * | 4/2005 | Hodges et al. ............ 204/403.14 |
| 7,045,054 | B1 | * | 5/2006 | Buck et al. .................... 205/778 |
| 2002/0027072 | A1 | * | 3/2002 | Cui et al. ..................... 204/403 |
| 2002/0053523 | A1 | * | 5/2002 | Liamos et al. ................ 205/787 |
| 2004/0045821 | A1 | * | 3/2004 | Cui et al. .................. 204/403.02 |
| 2005/0098433 | A1 | * | 5/2005 | Gundel .................... 204/403.02 |

FOREIGN PATENT DOCUMENTS

| DE | 101 17 868 A1 | 10/2002 |
| EP | 1067384 A2 | 1/2001 |
| EP | 1304566 A1 | 4/2003 |
| EP | 1327881 A1 | 7/2003 |
| EP | 1394535 A1 | 3/2004 |
| WO | 97/00441 | 1/1997 |

(Continued)

OTHER PUBLICATIONS

A Notice of Opposition to a European Patent filed by Abbott Diabetes Care Inc. on Jun. 6, 2011 regarding EP Patent No. 1747281.

(Continued)

*Primary Examiner* — Bach Dinh
(74) *Attorney, Agent, or Firm* — Larson & Anderson, LLC

(57) ABSTRACT

An electrochemical test device is provided having a base layer with a first electrode thereon and a top layer with a second electrode thereon. The two electrodes are separated by a spacer layer having an opening therein, such that a sample-receiving space is defined with one electrode on the top surface, the other electrodes on the bottom surface and side walls formed from edges of the opening in the spacer. Reagents for performing the electrochemical reaction are deposited on one of the electrodes and on the side walls of the sample-receiving space.

25 Claims, 5 Drawing Sheets

(56) References Cited

FOREIGN PATENT DOCUMENTS

| WO | 97/18464 | 5/1997 |
| WO | WO 98/35225 | 8/1998 |
| WO | WO 00/28068 | 5/2000 |
| WO | 01/75438 A2 | 10/2001 |
| WO | 03/056345 A1 | 7/2003 |
| WO | WO 03/069304 A2 | 8/2003 |
| WO | WO 2005/022143 | 3/2005 |
| WO | 2005108968 A1 | 11/2005 |

OTHER PUBLICATIONS

Minutes of the oral proceedings before the Opposition Division for European Patent No. EP-B-1 747 281, Proceeding held on May 16, 2013.

* cited by examiner glucose + GOXox ---> gluconolactone + GOXred

GOXred + 2 ferricyanide ---> GOXox + 2 ferrocyanide

ELECTROCHEMICAL ASSAY DEVICE AND RELATED METHODS

This application claims the benefit of U.S. Provisional Application No. 60/521,555 filed May 21, 2004, which application is incorporated herein by reference.

BACKGROUND OF THE INVENTION

This application relates to electrochemical assay devices in the form of single use test strips for detecting the presence or amount of an analyte in a sample and to methods of making and using such devices.

Single use disposable test strips for the electrochemical detection of analytes such as glucose are known. In such test strips, a sample is introduced into the test strip to contact at least two electrodes. Oxidation or reduction of the analyte is observed as a current generated between the two electrodes. Using glucose detection in a conduction cell as an example, as illustrated in FIG. 1, glucose is oxidized by the enzyme glucose oxidase to form gluconolactone and reduced enzyme. The oxidized form of the enzyme is regenerated by reaction with an oxidized mediator with the resulting generation of reduced mediator. This reduced mediator transfers an electron to one electrode, while at the other electrode electrons are transferred onto oxidized mediator, thus producing an observable current. FIG. 2 shows the observable current as a function of time in a test strip using an enzyme/mediator reagent system. In the figure, t=0 is the time of sample application. As shown, the current rises through a maximum, and then declines to reach an eventual steady state plateau. Measurements to determine the amount of analyte are taken after the maximum current has been reached, and generally at a time after the steady state has been achieved.

Before the maximum is reached in FIG. 2, there is a delay observed which can constitute a significant portion of the overall measurement time. The duration of this delay is dependent on the distance between the electrodes, and on the mobility of the mediator employed in the test strip. Mediator mobility is a property of the mediator itself, i.e., the diffusion coefficient, but is also dependent on other sample properties such as hematocrit and viscosity.

In order to increase user convenience, improvements to analyte test strips generally, and to glucose test strips in particular have focused on two major goals: shorter test times and smaller sample volumes. To some extent, these two goals have been achieved in tandem, since smaller sample volumes use smaller cells with smaller electrode-spacing, and smaller electrode-spacing results in shorter reaction time. These cells still have the current/time profile of FIG. 2, however, and thus built-in delay before a measurement can be taken. The present invention eliminates this delay, and thus provides a significant reduction in the time required to complete a test.

SUMMARY OF THE INVENTION

In accordance with the present invention, an electrochemical test device is provided having a base layer with a first electrode thereon and a top layer with a second electrode thereon. The two electrodes are separated by a spacer layer having an opening therein, such that a sample-receiving space is defined with one electrode on the top surface, the other electrodes on the bottom surface and side walls formed from edges of the opening in the spacer.

In a conduction cell where the reagents for performing the electrochemical reaction are deposited on one of the electrodes but not the side walls, the device produces a signal profile as in FIG. 2. In the device of the invention, the reagents are deposited not only on this electrode, but also on the side walls of the sample-receiving space. (FIG. 3) This results in a signal profile without the lag or with a reduced lag. (FIG. 4). In preferred embodiments, the reagents extend over the entire height of the side walls, although significant improvements are achievable with as little as 25% of the height of the side wall being coated with reagent.

The invention also provides a method of making test strips of the invention. In accordance with this method, an intermediate structure is formed comprising a base layer and a spacer layer disposed thereon. The base layer has the first electrode disposed thereon, and this electrode is exposed through an opening in the spacer layer. Thus, a well or channel is defined by the first electrode/base layer and the edges of the opening spacer layer. A liquid containing the reagents is introduced to the well or channel in such a way that it at least partially, and preferably completely, covers the side walls of the well. The liquid is then dried, leaving a coating of reagents on the bottom (first electrode) and side walls of the well/channel. Thereafter a top layer and a second electrode are added over the well/channel.

In a preferred embodiment of the method, the spacer layer has an adhesive coating and a release sheet on the side opposite the base layer and the side walls of the well extend upwards through the release sheet. Reagent material is introduced to the well/channel such that at least some part of the release sheet side wall is covered with the reagent-containing liquid prior to drying and preferably with reagent after drying. Subsequent removal of the release sheet results in a well in which the side walls are substantially completely covered with dried reagent.

DETAILED DESCRIPTION OF THE INVENTION

Figures 1, 2:
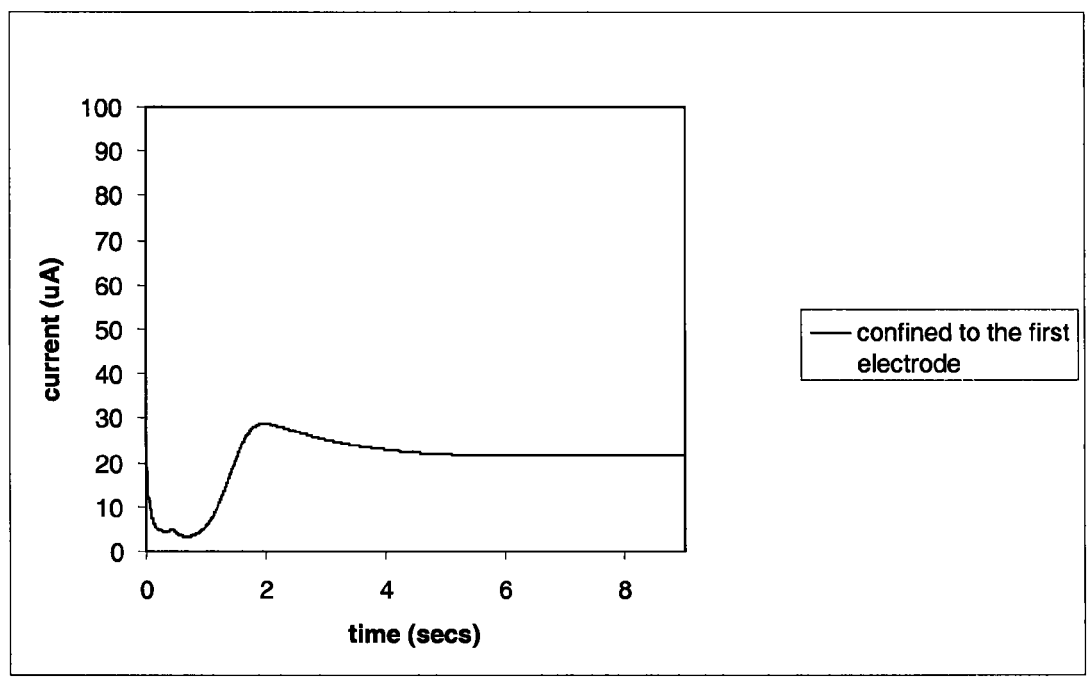
FIG. 1 shows the basic chemical reactions employed in a glucose test strip.
FIG. 2 shows current as a function of time in a conductance cell test strip with the reagents applied only to the bottom of the well.

The application relates to electrochemical test devices or strips, of the type commonly used in the assay of blood glucose.

Definitions

As used in the specification and claims of this application, the term "electrochemical test device" refers to a device which provides, alone or in combination with a reusable meter, a determination of an analyte in a sample using an electrochemical assay. Preferred electrochemical test devices are disposable single use devices of the type generally known for home determination of glucose levels.

The term "analyte" as used in the specification and claims of this application means a component of a sample to be measured. Non-limiting examples of specific analytes include glucose, hemoglobin, cholesterol, and vitamin C.

As used in the specification and claims of this application the term "electrode" refers to a component of the device which transfers electrons to or from species in a sample introduced into the sample-receiving space of the electrochemical test device, and which is or can be connected to circuitry to determine the amount of electron transfer occurring, either as a current flow or a potential difference between electrodes contacting the same sample. The electrodes in the devices of the invention are made from conductive materials consistent with the specific analyte that the electrochemical cell is intended to detect. Specific examples of suitable conductive electrode materials include gold, carbon, silver, palladium, and platinum. The conductive material used in the first and second electrodes may be the same or they may be different from one another. In a preferred embodiment of the present invention the conductive material used to form the electrodes is gold.

As used in the specification and claims of this application, the term "spacer" refers to a layer of material providing electrical separation between the two electrodes of the device. Thus, the spacer is a generally insulating material and electrical contact between the electrodes occurs only in the presence of a sample in the sample-receiving space. In preferred embodiments, the spacer is formed from a film or sheet of an insulating material. Examples of suitable materials include, without limitation, polyimide, polyester, polyethylene terephthalate (PET), polycarbonate, glass, and fiberglass. The spacer may also be formed by deposition of an insulating layer, for example by spraying on a resistive coating. Openings can be formed in such layers using conventional techniques including pre-cutting of an opening in a defined film or sheet, laser or chemical etching and the like.

As used in the specification and claims of this application, the term "reagent" refers to a chemical or mixture of chemicals that when combined with a sample allows the electrochemical test device to be used in making a determination of analyte in the sample. The reagent need not be sufficient to allow this determination, and addition of further chemicals to the sample prior to the introduction to the test device is acceptable, although not preferred. The reagent does, however, at a minimum contain a redox active material which is oxidized at the first electrode and reduced at the second electrode (or vice versa) when the device is used. The reagent may include multiple redox active materials which act as charge carrier between the electrodes.

As used in the specification and claims of this application, the phrase "determination of analyte" refers to and encompasses qualitative detection of the presence of the analyte, that is whether or not the analyte is present in detectable amounts in the sample, semiquantitative detection, that is whether or not the analyte is present in an amount greater than a predetermined threshold value, and quantitative evaluation, that is determination of the actual numerical amount of the analyte that is present.

As used in the specification and claims of this application, the terms "cover" or "covering" refers to coating of the specified surface. It does not require complete covering, for example in the case where pores may exist in the coating, but merely a distribution of the covering reagent over the specified surface. Further, it does not exclude coatings that may be less than complete due to unintentional flaws in the coating process in a specific device.

As used in the specification and claims of this application, the phrase "portion of the side walls extending contiguously from the covered electrode" refers to a coating where the reagent coating over the electrode flows into the reagent coating on the side walls.

Device of the Invention

Figure 3:
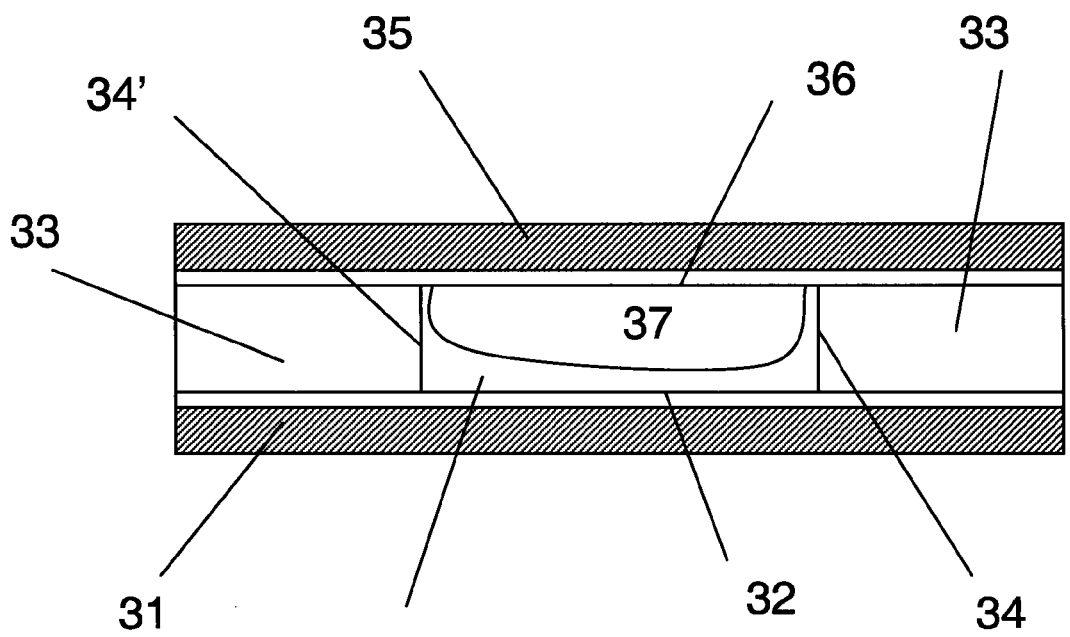
FIG. 3 shows a cross section through the sample-receiving space of a device in accordance with the invention.

FIG. 3 shows a cross section through the sample-receiving space of a device in accordance with the invention. As shown, a substrate layer 31 has an electrode 32 disposed thereon. Spacer layer 33 has an opening therein which provides side walls 34, 34'. Top substrate layer 35 has an electrode 36 disposed thereon. Sample receiving space 37 is bounded by electrodes 32 and 36 and side walls 34 and 34' and contains dried reagent 38. In an alternative embodiment, the sample receiving space may have top and bottom surfaces that are partially covered by the electrodes and partially exposed top layer. The dried reagent 38 covers the electrode 32 at the bottom of the sample receiving space 37 and extends upwards along the side walls 34, 34'.

Figure 4:
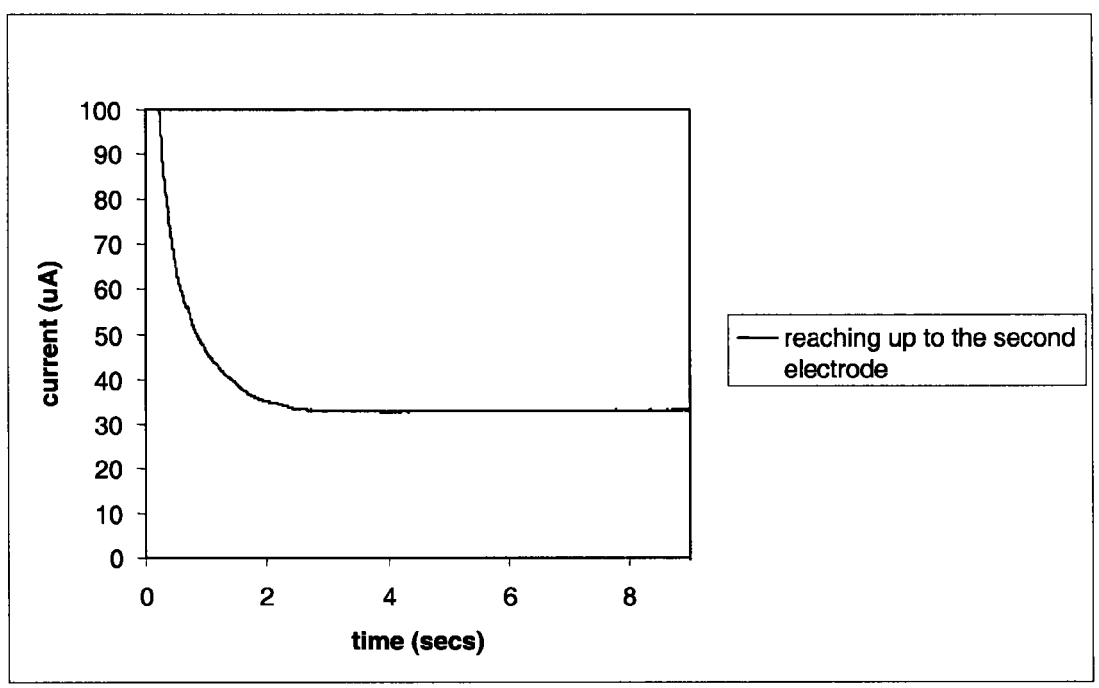
FIG. 4 shows current as a function of time in a test strip in accordance with the invention.

FIG. 4 shows a current/time profile for a device in accordance with the invention in which the dried reagent covers substantially all of the side walls. A comparison of this figure with FIG. 2 shows the clear advantage of the invention, namely that the current starts immediately, and steady state is achieved in less time.

While not intending to be bound to any specific mechanism, it is believed that this effect occurs because charge carriers are present in proximity to both electrodes from the outset, and therefore current can be generated immediately. In contrast, when the reagent is applied solely on the first electrode surface, the chemical reactions may commence immediately on sample addition but substantial current cannot flow until mediator (or some other redox active species) diffuses from the first electrode to the second. This takes time, and therefore there is a delay before an analyte-dependent current is observed. In addition, in the case of a reagent with a small amount of active mediator, the reaction cannot even commence beyond a certain point until a counter reaction is available. This delay in the onset of the chemical reaction is cumulative with delays due to other diffusion processes.

Based on this mechanism, theory predicts that the delay in time will be related to the square of the distance the charge carrier must travel to reach the second electrode. This means that if the distance between the dried reagent and the second electrode is cut in half, the time will be reduced by a factor of 4, and that even coating 25% of the side wall will result in a reduction in the time required to reach the current maximum by a factor of about 2. Thus, in the devices of the invention, at least 25%, preferably at least 50%, more preferably at least 75%, and most preferably all of the side wall extending above the first electrode is coated with dried reagent.

Figure 5:
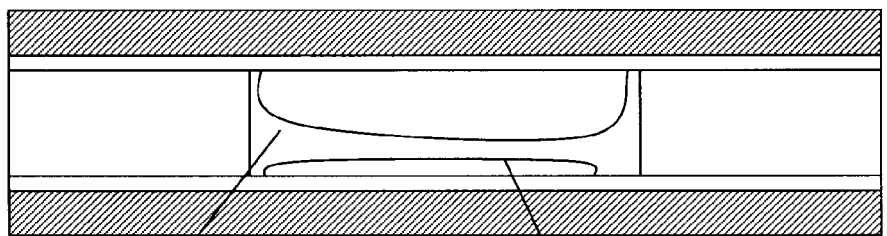
FIG. 5 shows a cross section through the sample-receiving space of a device in accordance with the invention.

This mechanism also makes it clear that the important component in the reagent is the mediator or charge carrier. Thus, as illustrated in FIG. 5, in an alternative embodiment of the invention, a reagent layer 51 comprising an enzyme such as glucose oxidase, is deposited on the surface of the first electrode, and a redox active coating 52 is deposited to cover the bottom and at least a portion of the sides of the sample-receiving space.

The redox active coating 52, or the reagent coating 38 may contain both redox states of the redox active species used in the device. This may be the reduced form, the oxidized form, or a mixture thereof. Specific non-limiting examples of redox active species are redox mediators known for use in glucose and other mediated electrochemical detection systems. The term "redox mediator" as used in the specification and claims of this application means a chemical species, other than the analyte, that is oxidized and/or reduced in the course of a multi-step process transferring electrons to or from the analyte to an electrode of the electrochemical cell. Non-limiting examples of mediators include:

ferricyanide
[FeIII(CN)5(ImH)]$^{2-}$
[FeIII(CN)5(Im)]$^{3-}$
[RuIII(NH3)5(ImH)]$^{3+}$
[RuIII(NH3)5(Im)]$^{2+}$
[FeII(CN)5(ImH)]$^{3-}$
[RuII(NH3)5(Im)H]$^{2+}$
[(NC)5FeII(Im)RuIII(NH3)5]$^{-}$
[(NC)5FeIII(Im)RuIII(NH3)5]$^{0}$
[(NC)5FeII(Im)RuII(NH3)5]$^{2-}$
Ferrocene (Fc) and derivatives including but not limited to:
Ferrocene monosulphonate
Ferrocene disulphonate
FcCO$_2$H
FcCH2CO$_2$H
FcCH:CHCO$_2$H
Fc(CH$_2$)$_3$CO$_2$H
Fc(CH$_2$)$_4$CO$_2$H
FcCH$_2$CH(NH$_2$)CO$_2$H
FcCH$_2$SCH$_2$CH(NH$_2$)CO$_2$H
FcCH$_2$CONH$_2$
Fc(CH$_2$)$_2$CONH$_2$
Fc(CH$_2$)$_3$CONH$_2$
Fc(CH$_2$)$_4$CONH$_2$
FcOH
FcCH$_2$OH
Fc(CH$_2$)$_2$OH
FcCH(Me)OH
FcCH$_2$O(CH$_2$)$_2$OH
1,1'-Fc(CH$_2$OH)$_2$
1,2-Fc(CH$_2$OH)$_2$
FcNH$_2$
FcCH$_2$NH$_2$
Fc(CH$_2$)$_2$NH$_2$
Fc(CH$_2$)$_3$NH$_2$
1,1'-Me$_2$FcCH$_2$NH$_2$
FcCH$_2$NMe$_2$
(R)-FcCH(Me)NMe$_2$
(S)-FcCH(Me)NMe$_2$
1,2-Me$_3$SiFcCH$_2$NMe$_2$
FcCH$_2$NMe$_3$
FcCH$_2$NH(CH$_2$)$_2$NH$_2$
1,1'-Me$_2$FcCH(OH)CH$_2$NH$_2$
FcCH(OH)CH$_2$NH$_2$
FcCH:CHCH(OH)CH$_2$NH$_2$
Fc(CH$_2$)$_2$CH(OH)CH$_2$NH$_2$
FcCH$_2$CH(NH$_2$)CH$_2$OH
FcCH$_2$CH(CH$_2$NH$_2$)CH$_2$OH
FcCH$_2$NH(CH$_2$)$_2$OH
1,1'-Me$_2$FcCHOCONHCH$_2$
FcCH(OH)(CH$_2$)$_2$NH$_2$
1,1'-Me$_2$FcCH(OH)CH$_2$NHAc
FcB(OH)$_3$
FCC$_6$H$_4$OPO$_3$Na$_2$
Osmium II and Osmium III tris(phenanthroline) (i.e. Os-phen) complexes including but not limited to:
Os(4,7-dmphen)$_3$
Os(3,4,7,8-tmphen)$_3$
Os(5,6-dmphen)$_3$
Os(bpy)$_3$Cl$_2$
Os(5-mphen)$_3$
Os(5-Cl-phen)$_3$
Os(5-NO$_2$-phen)$_3$
Os(5-phphen)$_3$
Os(2,9-dm-4,7-dpphen)$_3$
and isostructural ruthenium complexes including but not limited to:
Ru(4,7-dmphen)$_3$
Ru(3,4,7,8-tmphen)$_3$
Ru(5-mphen)$_3$
Ru(5,6-dmphen)$_3$
Ru(phen)$_3$
[Ru(4,4'-diNH$_2$-bipy)3]$^{2+}$
Osmium II and Osmium III tris(bipyridyl) complexes (i.e. Os(bpy)$_3$) including but not limited to:
Os(bpy)$_3$
Os(dmbpy)$_3$
and related ruthenium complexes, e.g.:
Ru(bpy)$_3$
Ru(4,4'-diNH$_2$-bpy)$_3$
Ru(4,4'-diCO$_2$Etbpy)$_3$
Osmium II and Osmium III bis(bipyridyl) (i.e. Os(bpy)$_2$) complexes with other ligands including but not limited to:
Os(bpy)$_2$dmbpy
Os(bpy)$_2$(HIm)$_2$
Os(bpy)$_2$(2MeHIm)$_2$
Os(bpy)$_2$(4MeHIm)$_2$
Os(dmbpy)$_2$(HIm)$_2$
Os(bpy)$_2$Cl(HIm)
Os(bpy)$_2$Cl(1-MeIm)
Os(dmbpy)$_2$Cl(HIm)
Os(dmbpy)$_2$Cl(1-MeIm)
and related ruthenium complexes, e.g.:
Ru(bpy)$_2$(5,5'diNH$_2$-bpy)
Ru(bpy)$_2$(5,5'diCO$_2$Etbpy)
Ru(bpy)$_2$(4,4'diCO$_2$Etbpy)
where Et is ethyl, bpy is bipyridyl, dmbpy is dimethyl bipyridyl, MeIm is N-methyl imidazole, MeHIm is methyl imidazole, HIm is imidazole, phen is phenanthroline, mphen is methyl phenantholine, dmphen is dimethyl phenanthroline, tmphen is tetramethyl phenanthroline, dmdpphen is dimethyl diphenyl phenanthroline, phphen is phenyl phenanthroline. In addition, it is understood that reduced or oxidized forms of these mediators may be used, either alone or in combination with each other.

Method of the Invention

Figure 6:
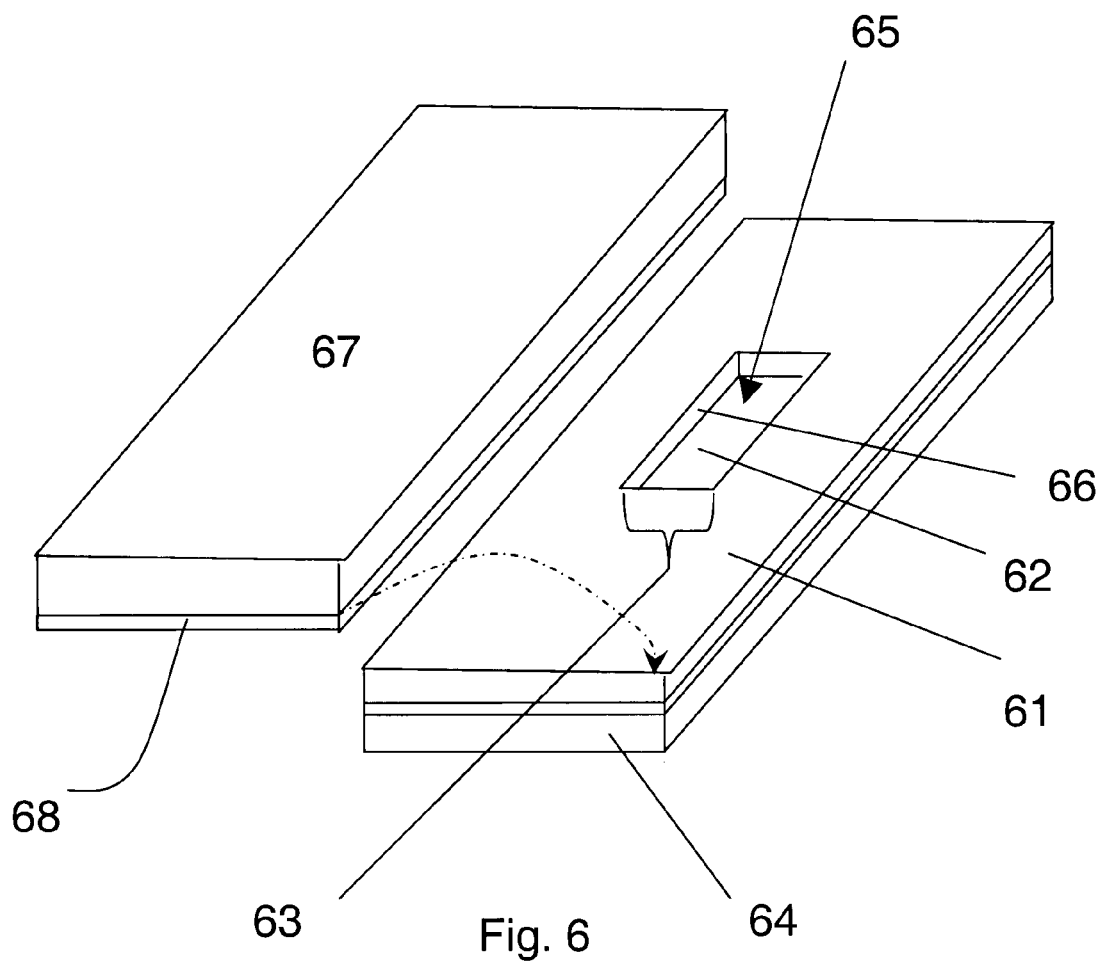
FIG. 6 shows a diagrammatic representation of the method of the invention.
Figure 7A:
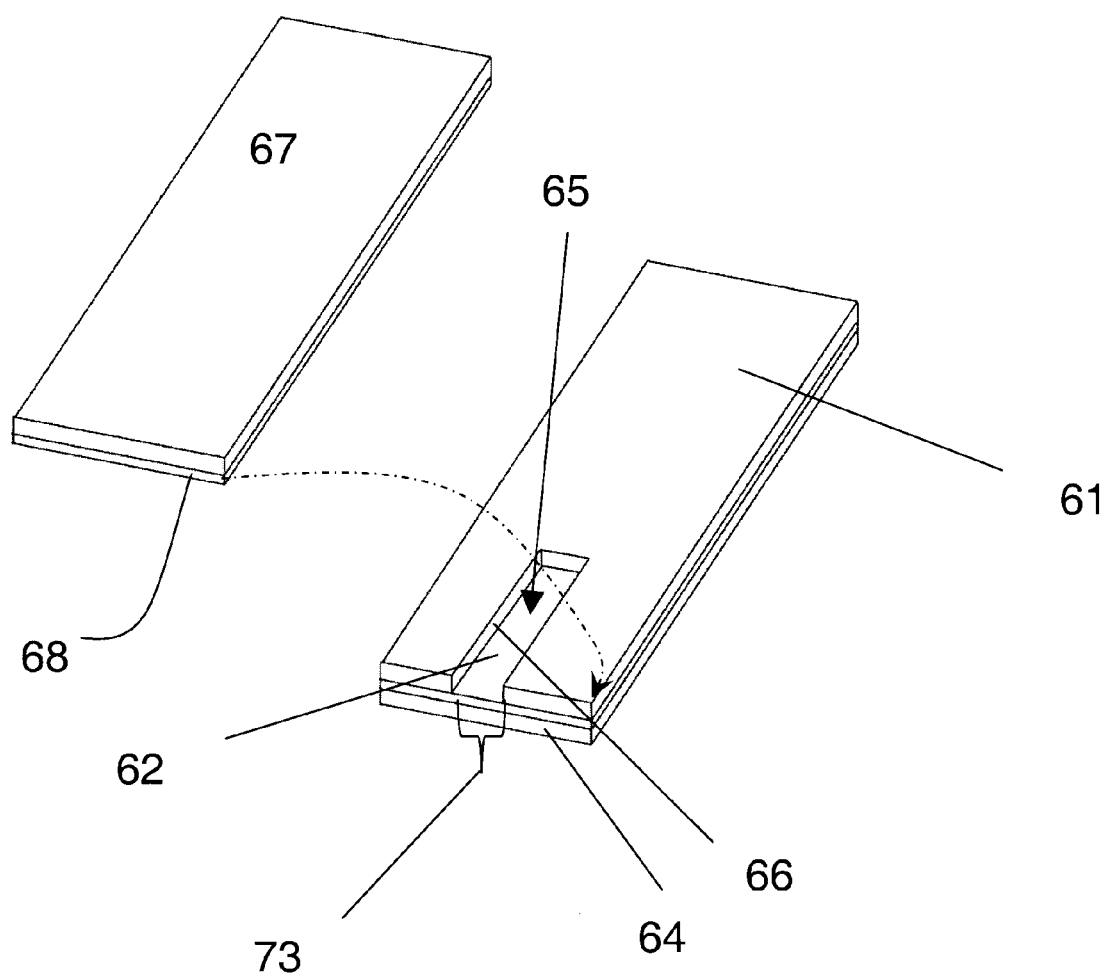
FIGS. 7A and B show diagrammatic representations of the method of the invention.
Figure 7B:
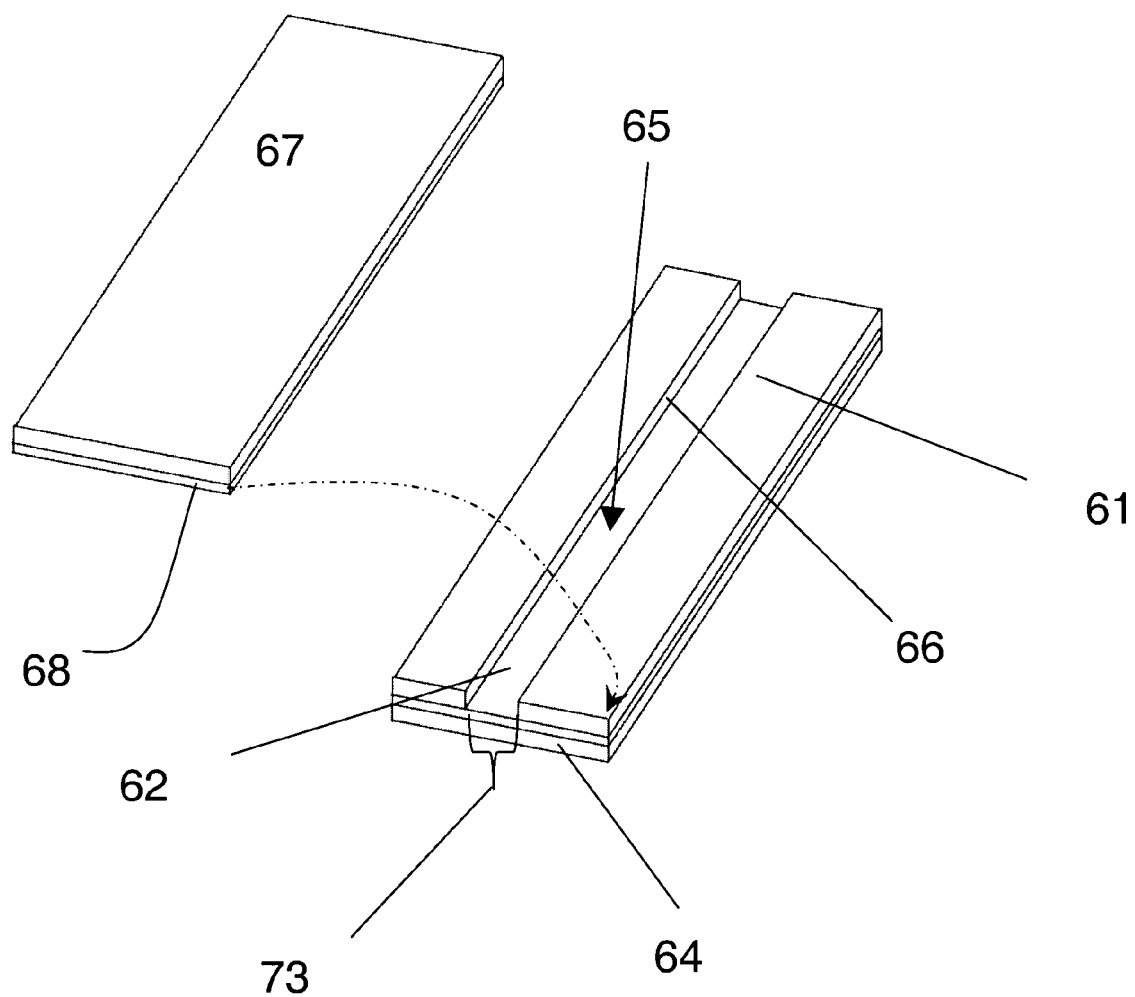

The present invention also provides a method of making an electrochemical test device of the type described above. This method is illustrated schematically in FIG. 6. As shown, a spacer layer 61 is disposed on a first electrode 62. This can be readily accomplished using an insulating film or sheet that is coated with adhesive on both sides of the spacer layer 61. The spacer layer 61 has an opening 63 through which the first electrode 62 is exposed. This opening can be in the form of a well 63 as depicted in FIG. 6, or as a channel 73 as shown in FIGS. 7A and B. An insulating support 64 is under the electrode 62.

A liquid reagent 65 comprising a redox active material is introduced into the opening 63/73 in the spacer layer 61 in such a way as to cover at least a portion of, but preferably all of, the exposed first electrode 62 and at least a portion of the side walls 66 of the opening 63/73. In one embodiment of the invention, this result is achieved by filling the opening 63/73 to a sufficient depth to at least partially cover the side walls. The result may also be achieved by applying the reagent along the electrode and side walls as a moving droplet on a dispensing tip so that it leaves a wetted trail, or using a ink jet or similar dispenser on a trajectory that results in wetted side walls as well as a wetted electrode. It should be noted that at the small scales generally employed in devices for glucose testing, the surface tension pulls the reagent to cover all wettted surfaces such that reagent surface area is minimized. This helps reagent spread into corners and up walls if already wetted.

The liquid reagent 65 is then dried in the opening 63/73 to form a dried reagent disposed in a layer covering the first electrode 62 and at least a portion of the side walls 66. The drying may be accomplished by simply leaving the structure to dry in air, drying in an applied air stream, heating, drying in a heated air stream, drying under vacuum, or drying in a heated vacuum. A sheet of material 67 with a conductive electrode surface 68 is then applied over the top of the spacer sheet, to form a second electrode facing the first electrode 62 across the opening 63. A sample introduction opening to the sample receiving space can be created by trimming the intermediate structure thus formed transversely through the opening 63/73 and contacts are formed with the electrodes to allow connection to an external meter. A preferred method for forming a device is described in U.S. Provisional Patent No. 60/521,555 and U.S. patent application Ser. No. 10/908,656 filed May 20, 2005, which is incorporated herein by reference.

EXAMPLE

Two devices were constructed using facing gold electrodes and a reagent comprising glucose oxidase, ferricyanide, buffer salts, and soluble stabilizers. In the device in accordance with the invention, the reagent extended up the side walls into proximity with the second electrode. In the control device, the reagent was disposed only on the first electrode. A 300 mV potential was applied (positive electrode was the first electrode with reagent; negative electrode was the second electrode without reagent) to each device as soon as the sample entered the strip (t=0). As shown in FIG. 2, in the control device the initial few seconds have no real current, and the current only increases beginning at about 1 sec. The current cannot increase significantly until the reagent can dissolve and diffuse to the second electrode, thereby providing a counter reaction to allow current to flow. FIG. 4 shows the current profile for the device in accordance with the invention. In this case, the reagent dissolves and diffuses almost as soon as the sample enters the strip and current begins to flow virtually immediately (t=0). Thus, a steady-state current is achieved in the sandwich geometry electrode structure of this device at about 3 seconds, as opposed to about 5 seconds for the other device.

What is claimed is:

1. An electrochemical test device comprising
a bottom substrate having a first electrode disposed thereon,
a top substrate having a second electrode disposed thereon,
a spacer disposed between the top and bottom substrates and having an opening therein, whereby a sample-receiving space is defined that has a bottom surface having the first electrode disposed thereon, a top surface, opposite the bottom surface, having the second electrode disposed thereon, and side walls formed from edges of the opening in the spacer; and
a reagent comprising a redox active material which disperses in a liquid sample placed in the sample-receiving space and is oxidized at the first electrode and reduced at the second electrode when the device is used;
wherein in the test device prior to introduction of a liquid sample, the reagent is disposed in a layer, a first part of said layer being disposed on and covering at least a portion of the first or second electrode and a second part of said layer being disposed upon and covering at least a portion of the side walls, wherein said second part of said layer extends on the side walls away from the first part of said layer such that the layer as a whole has a U-shaped cross section.

2. The device of claim 1, wherein the second part of the layer of reagent covers at least 25% of the height of the side walls.

3. The device of claim 1, wherein the second part of the layer of reagent covers at least 50% of the height of the side walls.

4. The device of claim 1, wherein the second part of the layer of reagent covers at least 75% of the height of the side walls.

5. The device of claim 1, wherein the second part of the layer of reagent covers 100% of the height of the side walls.

6. The device of claim 1, wherein the redox active material is selected from the group consisting of ferricyanide, [FeIII(CN)5(ImH)]$^{2-}$, [FeIII(CN)5(Im)]$^{3-}$, [RuIII(NH3)5(ImH)]$^{3+}$, [RuIII(NH3)5(Im)]$^{2+}$, [FeII(CN)5(ImH)]$^{3-}$, [RuII(NH3)5(Im)H]$^{2+}$, [(NC)5FeII(Im)RuIII(NH3)5]$^-$, [(NC)5FeIII(Im)RuIII(NH3)5]$^0$, [(NC)5FeII(Im)RuII(NH3)5]$^{2-}$, Ferrocene (Fc), Ferrocene monosulphonate, Ferrocene disulphonate, FcCO$_2$H, FcCH2CO$_2$H, FcCH:CHCO$_2$H, Fc(CH$_2$)$_3$ CO$_2$H, Fc(CH$_2$)$_4$CO$_2$H, FcCH$_2$CH(NH$_2$)CO$_2$H, FcCH$_2$SCH$_2$CH(NH$_2$)CO$_2$H, FcCH$_2$CONH$_2$, Fc(CH$_2$)$_2$CONH$_2$, Fc(CH$_2$)$_3$CONH$_2$, Fc(CH$_2$)$_4$CONH$_2$, FcOH, FcCH$_2$OH, Fc(CH$_2$)$_2$OH, FcCH(Me)OH, FcCH$_2$O(CH$_2$)$_2$OH, 1,1'-Fc(CH$_2$OH)$_2$, 1,2-Fc(CH$_2$OH)$_2$, FcNH$_2$, FcCH$_2$NH$_2$, Fc(CH$_2$)$_2$NH$_2$, Fc(CH$_2$)$_3$NH$_2$, 1,1'-Me$_2$FcCH$_2$NH$_2$, FcCH$_2$NMe$_2$, (R)-FcCH(Me)NMe$_2$, (S)-FcCH(Me)NMe$_2$, 1,2-Me$_3$SiFcCH$_2$NMe$_2$, FcCH$_2$NMe$_3$, FcCH$_2$NH(CH$_2$)$_2$NH$_2$, 1,1'-Me$_2$FcCH(OH)CH$_2$NH$_2$, FcCH(OH)CH$_2$NH$_2$, FcCH:CHCH(OH)CH$_2$NH$_2$, Fc(CH$_2$)$_2$CH(OH)CH$_2$NH$_2$, FcCH$_2$CH(NH$_2$)CH$_2$OH, FcCH$_2$CH(CH$_2$NH$_2$)CH$_2$OH, FcCH$_2$NH(CH$_2$)$_2$OH, 1,1'-Me$_2$FcCHOCONHCH$_2$, FcCH(OH)(CH$_2$)$_2$NH$_2$, 1,1'-Me$_2$FcCH(OH)CH$_2$NHAc, FcB(OH)$_3$, FcC$_6$H$_4$OPO$_3$Na$_2$, Os(4,7-dmphen)$_3$, Os(3,4,7,8-tmphen)$_3$, Os(5,6-dmphen)$_3$, Os(bpy)$_3$Cl$_2$, Os(5-mphen)$_3$, Os(5-Cl-phen)$_3$, Os(5-NO$_2$-phen)$_3$, Os(5-phphen)$_3$, Os(2,9-dm-4,7-dpphen)$_3$, Ru(4,7-dmphen)$_3$, Ru(3,4,7,8-tmphen)$_3$, Ru(5-mphen)$_3$, Ru(5,6-dmphen)$_3$, Ru(phen)$_3$, [Ru(4,4'-diNH$_2$-bipy)3]$^{2+}$, Os(bpy)$_3$, Os(dmbpy)$_3$, Ru(bpy)$_3$, Ru(4,4'-diNH$_2$-bpy)$_3$, Ru(4,4'-diCO$_2$Etbpy)$_3$, Os(bpy)$_2$dmbpy, Os(bpy)$_2$(HIm)$_2$, Os(bpy)$_2$(2MeHIm)$_2$, Os(bpy)$_2$(4MeHIm)$_2$, Os(dmbpy)$_2$(HIm)$_2$, Os(bpy)$_2$Cl(HIm), Os(bpy)$_2$Cl(1-MeIm), Os(dmbpy)$_2$Cl(HIm), Os(dmbpy)$_2$Cl(1-MeIm), Ru(bpy)$_2$(5,5'diNH$_2$-bpy), Ru(bpy)$_2$(5,5'diCO$_2$Etbpy), Ru(bpy)$_2$(4,4'diCO$_2$Etbpy), or the complementary redox forms (oxidized or reduced) thereof.

7. The device of claim 6, wherein the reagent further comprises glucose oxidase.

8. The device of claim 7, wherein the second part of the layer of reagent covers at least 25% of the height of the side walls.

9. The device of claim 7, wherein the second part of the layer of reagent covers at least 50% of the height of the side walls.

10. The device of claim 7, wherein the second part of the layer of reagent covers at least 75% of the height of the side walls.

11. The device of claim 7, wherein the second part of the layer of reagent covers 100% of the height of the side walls.

12. The device of claim 6, wherein the second part of the layer of reagent covers at least 25% of the height of the side walls.

13. The device of claim 6, wherein the second part of the layer of reagent covers at least 50% of the height of the side walls.

14. The device of claim 6, wherein the second part of the layer of reagent covers at least 75% of the height of the side walls.

15. The device of claim 6, wherein the second part of the layer of reagent covers 100% of the height of the side walls.

16. A method of making an electrochemical test device comprising the steps of:
   (a) forming a bottom substrate having a first electrode disposed thereon;
   (b) forming a spacer layer on the bottom substrate, said spacer layer having an opening formed therein through which the first electrode is exposed and side walls within the opening;
   (c) introducing a liquid reagent comprising a redox active material into the opening in the spacer layer,
   (d) drying the liquid reagent to form a dried reagent layer, wherein the liquid reagent is introduced to the opening in such a manner that upon drying a dried reagent layer is formed, said dried reagent layer having a first part covering at least a portion of the first electrode and a second part covering at least a portion of the side walls, wherein said second part of said layer extends on the side walls away from the first part of said layer such that the layer as a whole has a U-shaped cross section; and
   (e) placing a top substrate having a second electrode disposed thereon on the spacer layer aligned to have the second electrode facing the first electrode, thereby forming a sample-receiving space that has a first surface having the first electrode disposed thereon, a second surface, opposite the first surface, having the second electrode disposed thereon, and side walls formed from edges of the opening in the spacer.

17. The method of claim 16, wherein the second part of the layer of dried reagent covers at least 25% of the height of the side walls.

18. The method of claim 16, wherein the second part of the layer of dried reagent covers at least 50% of the height of the side walls.

19. The method of claim 16, wherein the second part of the layer of dried reagent covers at least 75% of the height of the side walls.

20. The method of claim 16, wherein the second part of the layer of dried reagent covers 100% of the height of the side walls.

21. The method of claim 16, wherein the spacer layer applied in step (b) comprises an adhesive coating and a release sheet disposed on the side of the spacer layer facing away from the first electrode, wherein an edge of the release sheet is aligned with the sidewall thereby increasing the height of the sidewall further comprising the step of removing the release sheet after drying of the liquid reagent to expose the adhesive layer.

22. The method of claim 21, wherein the liquid reagent is introduced to the opening in a volume sufficient to fill the opening to a level that at least partially covers the portion of the side walls formed from the release sheet.

23. The method of claim 16, wherein the liquid reagent is introduced in a volume sufficient to fill the opening to a level that partially covers the portion of the side walls of the opening.

24. The method of claim 16, wherein the opening and the bottom substrate form a well that is bounded by side walls on all sides.

25. The method of claim 16, wherein the opening and the bottom substrate form a channel bounded by side walls on only two opposing sides.

* * * * *